(12) United States Patent
Penning et al.

(10) Patent No.: US 7,462,724 B2
(45) Date of Patent: Dec. 9, 2008

(54) SUBSTITUTED 1H-BENZIMIDAZOLE-4-CARBOXAMIDES ARE POTENT PARP INHIBITORS

(75) Inventors: Thomas D. Penning, Elmhurst, IL (US);
Sheela A. Thomas, Libertyville, IL (US); Gui-Dong Zhu, Gurnee, IL (US);
Jianchun Gong, Deerfield, IL (US);
Vincent L. Giranda, Gurnee, IL (US);
Viraj B. Gandhi, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/560,166

(22) Filed: Nov. 15, 2006

(65) Prior Publication Data

US 2007/0112047 A1  May 17, 2007

Related U.S. Application Data

(60) Provisional application No. 60/736,928, filed on Nov. 15, 2005.

(51) Int. Cl.
*A61K 31/4184* (2006.01)
*C07D 235/18* (2006.01)
(52) U.S. Cl. .................. 548/310.7; 548/304.7; 514/394
(58) Field of Classification Search ............. 548/310.7, 548/304.7
See application file for complete search history.

(56) References Cited

U.S. PATENT DOCUMENTS 6,696,437 B1 * 2/2004 Lubisch et al. ......... 514/217.09

FOREIGN PATENT DOCUMENTS

| DE | 3522230 | 1/1987 |
|---|---|---|
| DE | 19916460 | 10/2000 |
| DE | 19920936 A1 | 11/2000 |
| JP | 200141067 | 5/2002 |
| WO | 09704771 | 2/1997 |
| WO | 9839343 | 9/1998 |
| WO | 0029384 | 5/2000 |
| WO | 0032579 | 6/2000 |
| WO | 0121615 | 3/2001 |
| WO | 0182877 | 11/2001 |
| WO | 02068407 | 9/2002 |
| WO | 03020698 | 3/2003 |
| WO | 03106430 | 12/2003 |
| WO | 2004065370 | 8/2004 |
| WO | 2004096793 | 11/2004 |
| WO | 0026192 | 5/2008 |

OTHER PUBLICATIONS

Burkart, V., et al., "Mice lacking the poly(ADP-ribose) polymerase gene are resistant to pancreatic beta-cell destruction and diabetes development induced by streptozocin", Nature Medicine, vol. 5, No. 3, pp. 314-319, 1999.

Chen, G., et al., "Potentiation of the antitumor activity of cisplatin in mice by 3-aminobenzamide and nicotinamide", Cancer Chemotherapy and Pharmacology, vol. 22, No. 4, pp. 303-307, 1988.

Cuzzocrea, S., et al., "Protective effects of 3-aminobenzamide, an inhibitor of poly (ADP-ribose) synthase in a carrageenan-induced model of local inflammation", European Journal of Pharmacology, vol. 342, pp. 67-76, 1998.

Ehrlich, W., et al., "Inhibition of the induction of collagenase by interleukin-1 β in cultured rabbit synovial fibroblasts after treatment with the poly(ADP-ribose)-polymerase inhibitor 3-aminobenzamide", Rheumatology International, vol. 15, pp. 171-172, 1995.

Kröger, H., et al., "Synergistic effects of thalidomide and poly(ADP-rose) polymerase inhibition on type Ii collagen-induced arthristis in mice", Inflammation, vol. 20, No. 2, pp. 203-215, 1996.

Prescott, et al., "Methods in Cell Biology," Academic Press, Inc, vol. XIV, pp. 33-71, 1976.

Szabó, C., et al., "Protection against peroxynitrite-induced fibroblast injury and arthritis, development by inhibition of poly(ADP-ribose) synthase", Proceedings of the National Academy of Sciences, vol. 95, pp. 3867-3872, 1998.

Thiemermann, C., et al., "Inhibition of the activity of poly(ADP ribose) synthetase reduces ischemia-reperfusion injury in the heart and skeletal muscle", Proceedings of the National Academy of Sciences, vol. 94, No. 2, pp. 679-683, 1997.

Weltin, D., et al., "Immunosuppressive Activities of 6(5H)-Phenanthridinone, A new Poly(ADP-Ribose)Polymerase Inhibitor," Int. J. Immunopharmac, vol. 17, No. 4, pp. 265-271, 1995.

White, A., et al., "Ptentiation of cytotoxic drug activity in human tumour cell lines, by amine-substituted 2-arylbenzimidazole-4-carboxamilde PARP-1 inhibitors," Bioorganic & Medicinal Chemistry Letters, vol. 14, No. 10, pp. 2433-2437, 2004.

Alexy, et al., "Inhibition of ADP-evoked platelet aggregation by selected poly(ADP-ribose)polymerase inhibitors", J Of Cardiovascular Pharm, 43(3), 423-431 (2004).

(Continued)

*Primary Examiner*—Laura L. Stockton
(74) *Attorney, Agent, or Firm*—Rachel A. Polster

(57) ABSTRACT

Compounds of Formula (I)

(I)

inhibit the PARP enzyme and are useful for treating a disease or a disorder associated with PARP. Also disclosed are pharmaceutical compositions comprising compounds of Formula (I), methods of treatment comprising compounds of Formula (I), and methods of inhibiting the PARP enzyme comprising compounds of Formula (I).

15 Claims, No Drawings

OTHER PUBLICATIONS

Gilchrist, "Cyclisation of Ortho-Substituted N-Arylbenzimidoyl Nitrenes, Part 2.1 Preferential Cyclizations at an Ortho-Position Bearing a Methoxycarbonyl Group", J of Chem Soci, Pekin Transactions 1, GB, Chemical Society. Letchworth, 2303-2307 (1979).

Griffin, et al., "Resistance Modifying Agents 3 Navel Benzimidazole and quinnazolinone Inhibitors of the DNA Repair Enzyme Poly(ADP-ribose)polymerase", Chemical Abstracts, 125(5), 43-47 (1996).

White, et al., "Potentiation of cytotoxic drug activity in human tumor cell lines, by amine-substituted 2-arylbenzimidazole-4carboxamide PARP-1 inhibitors", Bioorganic 7 medicinal Chemistry Letters, 14(10), 2433-2437 (2004).

STN Database Registry No. 784127-26-0, Nov. 19, 2004.
STN Database Registry No. 765258-50-2, Oct. 19, 2004.
STN Database Registry No. 748757-37-1, Seo. 21, 2004.
STN Database Registry No. 747397-72-4, Sep. 19, 2004.
STN Database Registry No. 739354-38-2, Sep. 5, 2004.
STN Database Registry No. 738569-62-5, Sep. 3, 2004.
STN Database Registry No. 687630-59-7, May 31, 2004.

* cited by examiner

SUBSTITUTED 1H-BENZIMIDAZOLE-4-CARBOXAMIDES ARE POTENT PARP INHIBITORS

This application claims priority from U.S. Provisional Ser. No. 60/736,928, filed Nov. 15, 2005.

TECHNICAL FIELD

The present invention relates to 1H-benzimidazole-4-carboxamides, their preparation, and their use as inhibitors of the enzyme poly(ADP-ribose)polymerase for the preparation of drugs.

BACKGROUND

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut and skeletal muscle. Inhibitors have been efficacious in inflammatory diseases such as arthritis, gout, inflammatory bowel disease, CNS inflammation such as MS and allergic encephalitis, sepsis, septic shock, hemmorhagic shock, pulmonary fibrosis, and uveitis. PARP inhibitors have also shown benefit in several models of degenerative disease including diabetes (as well as complications) and Parkinsons disease. PARP inhibitors can ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

SUMMARY OF THE INVENTION

In one embodiment, the present invention provides compounds of Formula (I)

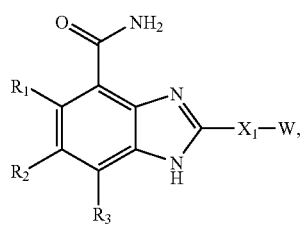

or a therapeutically acceptable salt, prodrug, or salt of a prodrug thereof, wherein $R_1$, $R_2$, and $R_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

$X_1$ is selected from the group consisting of aryl and heteroaryl, wherein $X_1$ is optionally substituted with 1, 2, 3, or 4 substituents selected from the group consisting of alkyl, cyano, halogen, and haloalkyl;

W is $X_2$—Y—$NR_6R_7$ or Y—$NR_6R_7$;

$X_2$ is selected from the group consisting of aryl and heteroaryl, wherein $X_2$ is optionally substituted with 1, 2, 3, or 4 substituents selected from the group consisting of alkyl, cyano, halogen, and haloalkyl;

Y is alkylenyl;

$R_6$ is selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heterocycle, heterocyclealkyl, heteroaryl, heteroarylalkyl, hydroxyalkyl, $(NR_CR_D)$alkyl, $(NR_CR_D)$carbonyl, $(NR_CR_D)$carbonylalkyl, and $(NR_CR_D)$sulfonyl;

$R_7$ is selected from the group consisting of cycloalkyl and cycloalkyl fused to phenyl, wherein $R_7$ may be optionally substituted with 1, 2, or 3 substituents selected from the group consisting of alkenyl, alkoxy, alkoxyalkyl, alkoxycarbonyl, alkoxycarbonylalkyl, alkyl, alkylcarbonyl, alkylcarbonylalkyl, alkynyl, carboxy, cycloalkyl, cycloalkylalkyl, cyano, haloalkoxy, haloalkyl, halogen, hydroxy, hydroxyalkyl, $NR_CR_D$, $(NR_CR_D)$alkyl, $(NR_CR_D)$carbonyl, $(NR_CR_D)$carbonylalkyl, $(NR_CR_D)$sulfonyl, and oxo; and $R_A$, $R_B$, $R_C$, and $R_D$ are independently selected from the group consisting of hydrogen, alkyl, and alkycarbonyl.

DETAILED DESCRIPTION OF THE INVENTION

In another embodiment, the present invention provides compounds of Formula (I)

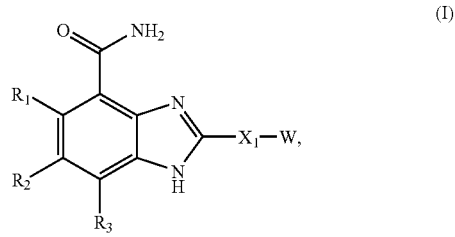

or a therapeutically acceptable salt, prodrug, or salt of a prodrug thereof, wherein $R_1$, $R_2$, and $R_3$ are independently selected from the group consisting of hydrogen and halogen;

$X_1$ is selected from the group consisting of aryl and heteroaryl, wherein $X_1$ is optionally substituted with halogen;

W is $X_2$—Y—$NR_6R_7$ or Y—$NR_6R_7$;

$X_2$ is aryl;

Y is alkylenyl;

$R_6$ is selected from the group consisting of hydrogen and alkyl; and $R_7$ is selected from the group consisting of cycloalkyl and cycloalkyl fused to phenyl.

In another embodiment, the present invention provides a pharmaceutical composition comprising a compound of Formula (I), wherein $R_1$, $R_2$, and $R_3$ are hydrogen.

In another embodiment, the present invention provides a pharmaceutical composition comprising a compound of Formula (I), wherein W is Y—NR$_6$R$_7$.

In another embodiment, the present invention provides a pharmaceutical composition comprising a compound of Formula (I), wherein R$_7$ is cycloalkyl.

In another embodiment, the present invention provides a pharmaceutical composition comprising a compound of Formula (I), wherein R$_6$ is hydrogen; and R$_7$ is cycloalkyl.

In another embodiment, the present invention provides a pharmaceutical composition comprising a compound of Formula (I), wherein X$_1$ is thiophenyl.

In another embodiment, the present invention provides a pharmaceutical composition comprising a compound of Formula (I), wherein X$_1$ is thiazolyl.

In another embodiment, the present invention provides a pharmaceutical composition comprising a compound of Formula (I), wherein X$_1$ is phenyl and X$_2$ is phenyl.

In another embodiment, the present invention provides a pharmaceutical composition comprising a compound of Formula (I), wherein X$_1$ is phenyl and W is Y—NR6R$_7$ In another embodiment, the present invention provides a pharmaceutical composition comprising a compound of Formula (I), wherein R$_2$ is halogen.

In another embodiment, the present invention provides a pharmaceutical composition comprising a compound of Formula (I), or a therapeutically acceptable salt thereof, in combination with a therapeutically acceptable carrier.

In another embodiment, the present invention provides a method of inhibiting PARP in a mammal in recognized need of such treatment comprising administering to the mammal a therapeutically acceptable amount of a compound of Formula (I) or a therapeutically acceptable salt thereof.

In another embodiment, the present invention provides a method of treating cancer in a mammal in recognized need of such treatment comprising administering to the mammal a therapeutically acceptable amount of a compound of Formula (I) or a therapeutically acceptable salt thereof.

In another embodiment, the present invention provides a method for decreasing tumor volume in a mammal in recognized need of such treatment comprising administering to the mammal a therapeutically acceptable amount of a compound of Formula (I) or a therapeutically acceptable salt thereof.

In another embodiment, the present invention provides a method of treating leukemia, colon cancer, glioblastomas, lymphomas, melanomas, carcinomas of the breast, or cervical carcinomas in a mammal in recognized need of such treatment comprising administering to the mammal a therapeutically acceptable amount of a compound of Formula (I) or a therapeutically acceptable salt thereof.

In another embodiment, the present invention provides a method of potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a method of potentiation of radiation therapy in a mammal in recognized need of such treatment comprising administering to the mammal a therapeutically acceptable amount of a compound of Formula (I) or a therapeutically acceptable salt thereof.

In another embodiment, the present invention provides a method of treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a method of reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a method of treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a method of treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a method of treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a method of treating hypoglycemia in a mammal in recognized need of such treatment comprising administering to the mammal a therapeutically acceptable amount of a compound of Formula (I) or a therapeutically acceptable salt thereof.

In another embodiment, the present invention provides a method of treating retroviral infection in a mammal in recognized need of such treatment comprising administering to the mammal a therapeutically acceptable amount of a compound of Formula (I) or a therapeutically acceptable salt thereof.

In another embodiment, the present invention provides a method of treating liver toxicity following acetominophen overdose in a mammal in recognized need of such treatment comprising administering to the mammal a therapeutically acceptable amount of a compound of Formula (I) or a therapeutically acceptable salt thereof.

In another embodiment, the present invention provides a method of treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a method of treating skin damage secondary to sulfur mustards in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for inhibiting the PARP enzyme in a mammal in recognized need of such treatment.

In another embodiment, the present invention provides a use of a compound of Formula (I), or a therapeutically acceptable salt thereof, to prepare a medicament for inhibiting tumor growth in a mammal in recognized need of such treatment.

In another embodiment, the present invention provides a use of a compound of Formula (I), or a therapeutically acceptable salt thereof, to prepare a medicament for treating cancer in a mammal in recognized need of such treatment.

In another embodiment, the present invention provides a use of a compound of Formula (I), or a therapeutically acceptable salt thereof, to prepare a medicament for treating leukemia, colon cancer, glioblastomas, lymphomas, melanomas, carcinomas of the breast, or cervical carcinomas in a mammal in a mammal in recognized need of such treatment.

In another embodiment, the present invention provides a use of a compound of Formula (I), or a therapeutically acceptable salt thereof, to prepare a medicament for potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for potentiation of radiation in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating hypoglycemia in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating retroviral infection in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating liver toxicity following acetaminophen overdose in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating skin damage secondary to sulfur mustards in a mammal in recognized need of such treatment comprising administering to the mammal a therapeutically acceptable amount of a compound of Formula (I) or a therapeutically acceptable salt thereof.

Definitions

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means at least one alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylenyl" as used herein, means a divalent group derived from a straight or branched chain hydrocarbon of from 1 to 6 carbon atoms. Representative examples include, but are not limited to, —$CH_2$—, —$CH(CH_3)$—, —$C(CH_3)_2$—, —$CH_2CH_2$—, —$CH_2CH_2CH_2CH_2CH_2$—, —$CH_2CH_2CH_2$—, —$CH_2CH(CH_3)CH_2$—.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a naphthyl group.

The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —$NR_ER_F$, and ($NR_ER_F$)carbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, 1-methyl-3-phenylpropyl, and 2-naphth-2-ylethyl.

The term "carbonyl" as used herein, means a —C(O)— group.

The term "carboxy" as used herein, means a —$CO_2H$ group.

The term "cyano" as used herein, means a —CN group.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycloalkyl groups of the present invention are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, oxo, —$NR_ER_F$, and ($NR_ER_F$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring is fused to another 5 or 6 membered heteroaryl ring. Nitrogen heteroatoms contained within the heteroaryl may be optionally oxidized to the N-oxide. The heteroaryl is connected to the parent molecular moiety through any carbon atom contained within the heteroaryl while maintaining proper valence. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thienopyridinyl, thienyl, triazolyl, and triazinyl.

The heteroaryl groups of the present invention are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —NR$_E$R$_F$, and (NR$_E$R$_F$)carbonyl.

The term "heteroarylalkyl" as used herein, means a heteroaryl, as defined herein, appended to the parent molecular moiety through an alkyl group, as defined herein. Representative examples of heteroarylalkyl include, but are not limited to, pyridinymethyl.

The term "heterocycle" or "heterocyclic" as used herein, means a monocyclic or bicyclic heterocyclic ring. The monocyclic heterocyclic ring consists of a 3, 4, 5, 6, 7, or 8 membered ring containing at least one heteroatom independently selected from O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocyclic ring consists of a monocyclic heterocyclic ring fused to a cycloalkyl group or the monocyclic heterocyclic ring fused to a phenyl group or the monocyclic heterocyclic ring fused to another monocyclic heterocyclic ring. The heterocycle is connected to the parent molecular moiety through any carbon or nitrogen atom contained within the heterocycle while maintaining proper valence. Representative examples of heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The heterocycles of this invention are substituted with 0, 1, 2, or 3 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —NR$_E$R$_F$, and (NR$_E$R$_F$)carbonyl.

The term "heterocyclealkyl" as used herein, means a heterocycle, as defined herein, appended to the parent molecular moiety through an alkyl group, as defined herein.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "nonaromatic" as used herein, means that a 4 membered nonaromatic ring contains zero double bonds, a 5 membered nonaromatic ring contains zero or one double bond, a 6, 7, or 8 membered nonaromatic ring contains zero, one, or two double bonds.

The term "NR$_A$R$_B$" as used herein, means two groups, R$_A$ and R$_B$, which are appended to the parent molecular moiety through a nitrogen atom. R$_A$ and R$_B$ are each independently hydrogen, alkyl, and alkylcarbonyl. Representative examples of NR$_A$R$_B$ include, but are not limited to, amino, methylamino, acetylamino, and acetylmethylamino.

The term "(NR$_A$R$_B$)carbonyl" as used herein, means a NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "NR$_C$R$_D$" as used herein, means two groups, R$_C$ and R$_D$, which are appended to the parent molecular moiety through a nitrogen atom. R$_C$ and R$_D$ are each independently hydrogen, alkyl, and alkylcarbonyl. Representative examples of NR$_A$R$_D$ include, but are not limited to, amino, methylamino, acetylamino, and acetylmethylamino.

The term "(NR$_C$R$_D$)carbonyl" as used herein, means a NR$_C$R$_D$ group, as defined herein, appended to the parent molecular moiety through a carbonyl group, as defined herein. Representative examples of (NR$_C$R$_D$)carbonyl include, but are not limited to, aminocarbonyl, (methylamino)carbonyl, (dimethylamino)carbonyl, and (ethylmethylamino)carbonyl.

The term "(NR$_C$R$_D$)carbonylalkyl" as used herein, means a (NR$_C$R$_D$)carbonyl group, as defined herein, appended to the parent molecular moiety through an alkyl group, as defined herein.

The term "(NR$_C$R$_D$)sulfonyl" as used herein, means a NR$_C$R$_D$ group, as defined herein, appended to the parent molecular moiety through a sulfonyl group, as defined herein. Representative examples of (NR$_C$R$_D$)sulfonyl include, but are not limited to, aminosulfonyl, (methylamino)sulfonyl, (dimethylamino)sulfonyl, and (ethylmethylamino)sulfonyl.

The term "NR$_E$R$_F$" as used herein, means two groups, R$_E$ and R$_F$, which are appended to the parent molecular moiety through a nitrogen atom. R$_E$ and R$_F$ are each independently hydrogen, alkyl, and alkylcarbonyl. Representative examples of NR$_E$R$_F$ include, but are not limited to, amino, methylamino, acetylamino, and acetylmethylamino.

The term "(NR$_E$R$_F$)carbonyl" as used herein, means a NR$_E$R$_F$ group, as defined herein, appended to the parent molecular moiety through a carbonyl group, as defined herein. Representative examples of (NR$_E$R$_F$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

Compounds of the present invention can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named by ACD/ChemSketch version 5.06 (developed by Advanced Chemistry Development, Inc., Toronto, ON, Canada) or were given names which appeared to be consistent with ACD nomenclature.

Determination of Biological Activity

Inhibition of PARP

Nicotinamide[2,5',8-3H]adenine dinucleotide and strepavidin SPA beads were purchased from Amersham Biosiences (UK) Recombinant Human Poly(ADP-Ribose) Polymerase (PARP) purified from *E. coli* and 6-Biotin-17—$NAD^+$, were purchase from Trevigen, Gaithersburg, Md. $NAD^+$, Histone, aminobenzamide, 3-amino benzamide and Calf Thymus DNA (dcDNA) were purchased from Sigma, St. Louis, Mo. Stem loop oligonucleotide containing MCAT sequence was obtained from Qiagen. The oligos were dissoloved to 1 mM in annealing buffer containing 10 mM Tris HCl pH 7.5, 1 mM EDTA, and 50 mM NaCl, incubated for 5 min at 95° C., and followed by annealing at 45° C. for 45 minutes. Histone H1 (95% electrophoretically pure) was purchased from Roche, Indianapolis, Ind. Biotinylated histone H1 was prepared by treating the protein with Sulfo-NHS-LC-Biotin from Pierce Rockford, Ill. The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 min followed by subsequent 4° C. incubation for 1 hr. Streptavidin coated (FlashPlate Plus) microplates were purchased from Perkin Elmer, Boston, Mass.

PARP1 assay was conducted in PARP assay buffer containing 50 mM Tris pH 8.0, 1 mM DTT, 4 mM $MgCl_2$. PARP reactions contained 1.5 μM [$^3$H]-$NAD^+$ (1.6 uCi/mmol), 200 nM biotinylated histone H1, 200 nM s1DNA, and 1 nM PARP enzyme. Auto reactions utilizing SPA bead-based detection were carried out in 100 μl volumes in white 96 well plates. Reactions were initiated by adding 50 μl of 2× $NAD^+$ substrate mixture to 50 μl of 2× enzyme mixture containing PARP and DNA. These reactions were terminated by the addition of 150 μl of 1.5 mM benzamide (~1000-fold over its IC50). 170 μl of the stopped reaction mixtures were transferred to streptavidin Flash Plates, incubated for 1 hr, and counted using a TopCount microplate scintillation counter. The $K_i$ data was determined from inhibition curves at various substrate concentrations and are shown in Table 1 for compounds of the present invention

TABLE 1

| Inhibition of PARP (nM) | | | | | | | |
|---|---|---|---|---|---|---|---|
| 17 | 4.4 | 13.7 | 20.3 | 9.8 | 4 | 8.6 | 4.6 |
| 15.2 | 5.1 | 9 | 1.5 | 9 | 2.2 | 11.8 | 14.3 |
| 69 | 17.5 | 4.7 | 7.3 | 2.3 | 6.4 | 19 | 28 |
| 20 | 22 | 14 | | | | | |

Cellular PARP Assay:

C41 cells were treated with a compound of the present invention for 30 minutes in 96 well plate. PARP was then activated by damaging DNA with 1 mM $H_2O_2$ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-tween (0.05%) (blocking solution) for 30 minutes at room temperature. The cells were incubated with anti-PAR antibody 10H (1:50) in Blocking solution at 37° C. for 60 minutes followed by washing with PBS-Tween20 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-Tween20 5 times, the analysis was performed using an fmax Fluorescence Microplate Reader (Molecular Devices, Sunnyvalle, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of the present invention penetrate cell membranes and inhibit PARP in intact cells. The $EC_{50s}$ for representative compounds of the present invention are provided in Table 2.

TABLE 2

| Cellular Activity $EC_{50}$ (nM) | | | | | | |
|---|---|---|---|---|---|---|
| 2.9 | 1.2 | 70 | 29 | 7.5 | 1.5 | 55 |
| 23 | 61 | 79 | 0.9 | 6 | 4.7 | 19.5 |
| 3.4 | 6.3 | 10.8 | 2 | 19.8 | 13 | 3.7 |
| 2 | 89 | 62 | 62 | | | |

As PARP inhibitors, the compounds of the present invention have numerous therapeutic applications related to, ischemia reperfusion injury, inflammatory diseases, degenerative diseases, protection from adverse effects of cytotoxic compounds, and potentiation of cytotoxic cancer therapy. In particular, compounds of the present invention potentiate radiation and chemotherapy by increasing cell death of cancer cells, limiting tumor growth, decreasing metastasis, and prolonging the survival of tumor-bearing mammals. Compounds of Fomula (I) can treat leukemia, colon cancer, glioblastomas, lymphomas, melanomas, carcinomas of the breast, and cervical carcinomas.

Other therapeutic applications include, but are not limited to, retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetominophen overdose, cardiac and kidney toxicities from doxorubicin and platinum based antineoplastic agents, and skin damage secondary to sulfur mustards. (G. Chen et al. Cancer Chemo. Pharmacol. 22 (1988), 303; C. Thiemermann et al., Proc. Natl. Acad. Sci. USA 94 (1997), 679-683 D. Weltin et al. Int. J. Immunopharmacol. 17 (1995), 265-271; H. Kröger et al. Inflammation 20 (1996), 203-215; W. Ehrlich et al. Rheumatol. Int. 15 (1995), 171-172; C. Szabo et al., Proc. Natl. Acad. Sci. USA 95 (1998), 3867-3872; S. Cuzzocrea et al. Eur. J. Pharmacol. 342 (1998), 67-76; V. Burkhart et al., Nature Medicine (1999), 5314-19).

When used in the above or other treatments, a therapeutically effective amount of one of the compounds of the present invention can be employed as a zwitterion or as a pharmaceutically acceptable salt. By a "therapeutically effective amount" of the compound of the invention is meant a sufficient amount of the compound to treat or prevent a disease or disorder ameliorated by a PARP inhibitor at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

The term "pharmaceutically acceptable salt" is meant to include those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the present invention or separately by reacting the free base of a compound of the present invention with a suitable acid. Representative acids include, but are not limited to acetatic, citric, aspartic, benzoic, benzenesulfonic, butyric, fumaric, hydrochloric, hydrobromic, hydroiodic, lactic, maleic, methanesulfonic, pamoic, pectinic, pivalic, propionic, succinic, tartaric, phosphic, glutamic, and p-toluenesulfonic. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained.

A compound of the present invention may be administered as a pharmaceutical composition containing a compound of the present invention in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions can be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or non-aqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions can also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Total daily dose of the compositions of the invention to be administered to a human or other mammal host in single or divided doses may be in amounts, for example, from 0.0001 to 300 mg/kg body weight daily and more usually 1 to 300 mg/kg body weight. The dose, from 0.0001 to 300 mg/kg body, may be given twice a day.

Abbreviations which have been used in the descriptions of the examples that follow are: DBU for 1,8-diazabicyclo [5.4.0]undec-7-ene; DMF for N,N-dimethylformamide; DMSO for dimethylsulfoxide; $Et_2O$ for diethyl ether; EtOAc for ethyl acetate; EtOH for ethanol; HPLC for high pressure liquid chromatography; LDA for lithium diisopropylamide; MeOH for methanol; psi for pounds per square inch; TFA for trifluoroacetic acid; THF for tetrahydrofuran, and TMS for trimethylsilane.

Compounds having formula I may be made by synthetic chemical processes, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary.

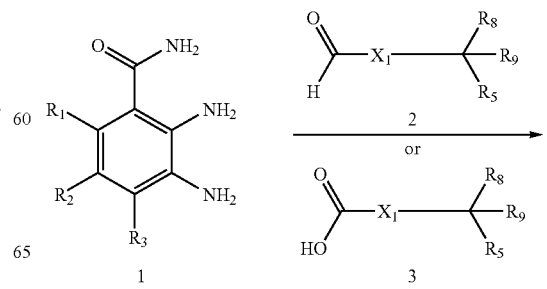

Scheme 1

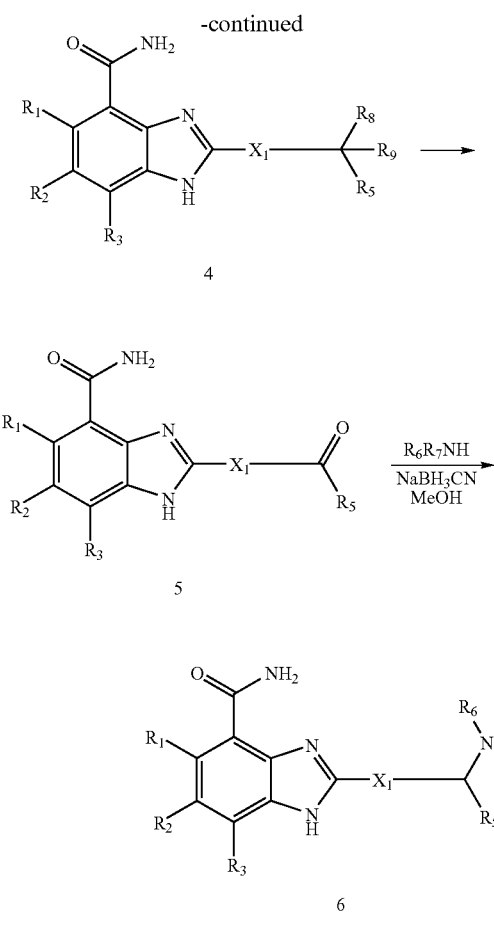

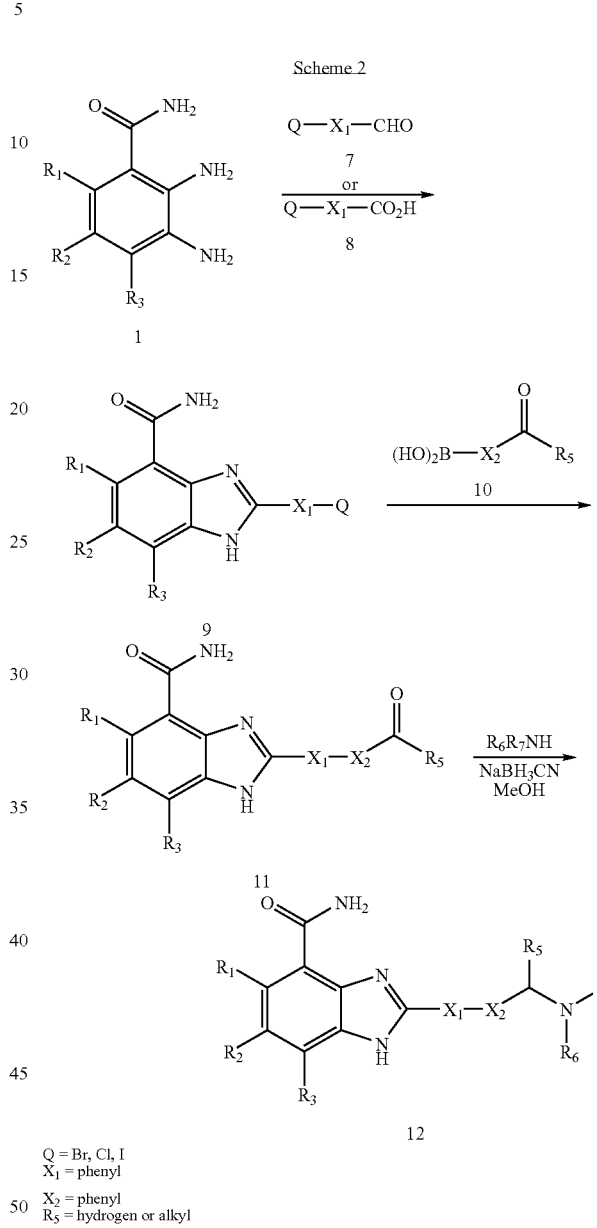

Q = Br, Cl, I
$X_1$ = phenyl
$X_2$ = phenyl
$R_5$ = hydrogen or alkyl

As shown in Scheme 1, compounds of formula 6 which are representative of compounds of formula (I), wherein $X_1$ is phenyl or thiophenyl and W is Y—$NR_6R_7$ may be prepared as outlined. Accordingly, when a mixture of compounds of formula 1 and compounds of formula 2 wherein $R_5$ is hydrogen or alkyl, $R_8$ and $R_9$ are both an alkyl acetal or $R_8$ and $R_9$ taken together form a cyclic acetal, or $R_8$ and $R_9$ together form oxo, are heated in the presence of an acid or under conditions such as refluxing methanol containing Pd/C will provide compounds of formula 4 (or formula 5 if starting with an unprotected ketone or aldehyde). Alternatively, compounds of formula 1 when treated with compounds of formula 3 (containing a protected or unprotected ketone or aldehyde similar to compounds of formula 2) using standard amide forming reagents, such as 1,1'-carbonyldiimidazole (CDI), will provide an intermediate amide, which when treated with an acid, such as acetic acid under heated conditions will provide compounds of formula 4 (or 5 if starting with an unprotected ketone or aldehyde). When compounds of formula 4 containing a protected ketone or aldehyde such as a ketal or acetal are treated with a catalytic amount of an acid-such as acetic, dilute hydrochloric or sulfuric acid will provide compounds of formula 5. Compounds of formula 5 when treated with amines $R_6R_7NH$ in the presence of a reducing agent, such as but not limited to sodium cyanoborohydride or other conditions known to one skilled in the art that will effect a reductive amination, will provide compounds of formula 6 which are representative of compounds of the present invention.

As outlined in Scheme 2, compounds of formula 12 which are representative of compounds of formula (I) wherein both $X_1$ and $X_2$ are phenyl may be prepared accordingly. Compounds of formula 1 when treated with compounds of formula 7 or of formula 8, wherein $X_1$ is phenyl and Q is chloro, bromo or iodo, according to the conditions outlined in Scheme 1, which are used to generate benzamidazoles, will provide compounds of formula 9. Furthermore, compounds of formula 9 when treated with boronic acids of formula 10, wherein $X_2$ is phenyl in the presence of a palladium catalyst such as but not limited to [1,1'-bis(diphenylphosphino)ferrocene]dichloro palladium and sodium carbonate under heated conditions will provide compounds of formula 11. Compounds of formula 11 when treated with amines of formula $R_6R_7NH$ under reductive amination conditions known to one skilled in the art, or as outlined in Scheme 1, will provide compounds of formula 12.

The following Examples are intended as an illustration of and not a limitation upon the scope of the invention as defined in the appended claims. The compounds of this invention can be prepared by a variety of synthetic routes.

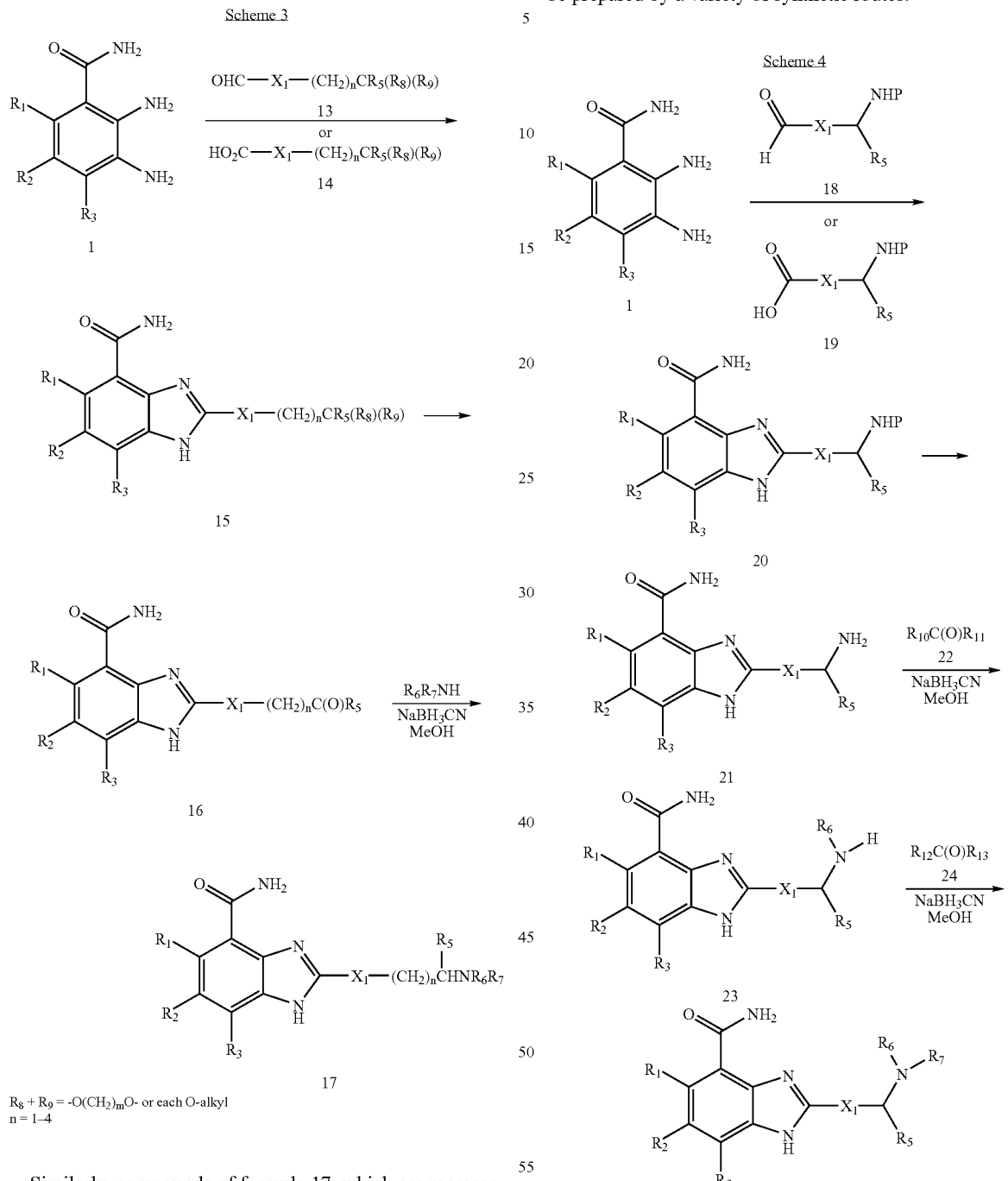

$R_8 + R_9 = -O(CH_2)_mO-$ or each O-alkyl
n = 1-4

Similarly, compounds of formula 17, which are representative of compounds of formula (I), wherein $X_1$ is phenyl and W is $Y-NR_6R_7$ are synthesized accordingly. Compounds of formula 1 when treated with compounds of formula 13 or 14, wherein $R_8$ and $R_8$ are each —O— alkyl or together form a cyclic acetal, according to the procedures outlined in Scheme 1, will provide compounds of formula 15. The acetal group of compounds of formula 15 can be deprotected under acid-catalyzed conditions to provide compounds of formula 16. Compounds of formula 16 when treated to reductive amination conditions as outlined in Scheme 1 or 2 will provide compounds of formula 17.

Scheme 4

Scheme 4 shows the synthesis of compounds of formula 22 where $X_1$ is thiazolyl and W is $Y-NR_6R_7$. Compounds of formula 1 may be coupled to compounds of formula 18 (containing an amine with a protecting group P) using, for example, Pd/C or sodium bisulfite, with heating, to give compounds of formula 20. Alternatively, compounds of formula 1 may be coupled to compounds of formula 19 (containing an amine with a protecting group P) using standard amide forming reagents, such as 1,1'-carbonyldiimidazole (CDI), to give the intermediate amide, which was treated with acid, such as acetic acid, with heating, to provide compounds of formula 20. Deprotection of the amine provided compounds of the formula 21. Compounds of formula 21 may under go reductive amination with a ketone or aldehyde 22 using conditions known to those of ordinary skill in the art to give compounds of formula 23. Compounds of formula 23 may optionally under go a second reductive amination with a ketone or aldehyde 24 to give compounds of formula 25.

The following Examples are intended as an illustration of and not a limitation upon the scope of the invention as defined in the appended claims. The compounds of this invention can be prepared by a variety of synthetic routes.

EXAMPLE 1

2-{4-[1-(cyclohexylmethylamino)ethyl]phenyl}-1H-benzimidazole-4-carboxamide

EXAMPLE 1A 2-(4-acetylphenyl)-1H-benzimidazole-4-carboxamide

4-Acetylbenzoic acid (1.64 g, 10 mmol) in N, N-dimethylformamide (DMF, 10 mL) and pyridine (10 mL) was stirred at 40° C. for 10 minutes. 1,1'-carbonyldiimidazole (CDI, 1.7 g, 10.5 mmol) was added and the mixture was stirred at 40° C. for 30 minutes. 2,3-diaminobenzamide dihydrochloride (synthesized as described in U.S. Pat. No. 6,737,421, column 11, EXAMPLE 2, step (e), 2.2 g, 10 mmol) was added and the mixture was stirred at ambient temperature for 2.5 hours. Isopropyl alcohol (20 mL) was added and the mixture was stirred at ambient temperature for 20 hours. The resulting solid was filtered, washed with isopropyl alcohol and dried to give 2.1 g of a bright yellow solid. The crude material was stirred in water (30 ML) with 50% sodium hydroxide (1 mL) at ambient temperature for 7.5 hours. The solution was filtered and the solid (1.84 g) collected and stirred in refluxing acetic acid (25 mL) for 4 hours. The mixture was concentrated, stirred in dichloromethane, filtered, and dried to provide 1.78 g (64% for 2 steps) of the title compound. $^1$H NMR (DMSO-$d_6$) δ 9.27 (br, 1H), 8.40 (d, J=8.4 Hz, 2H), 8.16 (d, J=8.5 Hz, 2H), 7.89 (d, J=7.5 Hz, 1H), 7.78 (d, J=6.8 Hz, 1H), 7.78 (br, 1H), 7.37 (t, J=7.8 Hz, 1H), 2.66 (s, 3H).

EXAMPLE 1B

2-{4-[1-(cyclohexylmethylamino)ethyl]phenyl}-1H-benzimidazole-4-carboxamide

A solution of EXAMPLE 1A (0.1 g, 0.4 mmol) and cyclohexylmethylamine (0.2 mL, 1.5 mmol) in methanol (1 mL) was treated with sodium cyanoborohydride (0.05 g, 0.8 mmol) and acetic acid (0. 1 mL). The mixture was stirred at 70° C. for 72 hours then concentrated. The residue was purified by HPLC on a C18 column with 0-100% acetonitrile/water/0.1% trifluoroacetic acid to provide the title compound as the trifluoroacetate salt. $^1$H NMR (DMSO-$d_6$) δ 9.25 (s, 1H), 8.35 (s, 2H), 7.89 (s, 1H), 7.78 (s, 4H), 7.35-7.40 (m, 1H), 4.76 (s, 1H), 3.35 (s, 6H), 2.82 (d, J=4.9 Hz, 1H), 2.46 (d, J=5.2 Hz, 1H), 1.69 (s, 2H), 1.66 (d, J=6.4 Hz, 3H), 1.37 (s, 2H), 1.09 (s, 1H).

EXAMPLE 2

2-[4-(1-cyclobutylaminoethyl)phenyl]-1H-benzimidazole-4-carboxamide

A solution of EXAMPLE 1A (0.07 g, 0.3 mmol) and cyclobutylamine (0.34 mL, 4.8 mmol) in methanol (1 mL) was treated with sodium cyanoborohydride (0.016 g, 0.3 mmol) and acetic acid (0.2 mL). The mixture was stirred at ambient temperature for 48 hours then concentrated. The residue was purified by chromatography on a silica gel column with 0-10% methanol/dichloromethane/0.1% ammonium hydroxide to provide the title compound. $^1$H NMR (DMSO-$d_6$) δ 9.34 (s, 1H), 8.19 (d, J=7.7 Hz, 2H), 7.86 (d, J=7.7 Hz, 1H), 7.72 (d, J=8.0 Hz, 2H), 7.57 (d, J=7.7 Hz, 2H), 7.34 (t, J=7.7 Hz, 1H), 3.97 (s, 1H), 3.16 (d, J=5.2 Hz, 4H), 2.09 (s, 1H), 1.88 (s, 2H), 1.75 (s, 1H), 1.60 (s, 1H), 1.52 (s, 1H), 1.36 (s, 3H).

EXAMPLE 3

2-{4'-[(cyclohexylmethylamino)methyl]biphenyl-4-yl}-1H-benzimidazole-4-carboxamide

EXAMPLE 3A 2-(4-bromophenyl)-1H-benzimidazole-4-carboxamide

To a mixture of 2,3-diaminobenzamide dihydrochloride (synthesized as described in U.S. Pat. No. 6,737,421, column 11, EXAMPLE 2, step (e), 5 g, 22.3 mmol) and 4-bromobenzaldehyde (4.13 g, 22.3 mmol) in methanol (200 mL) was added 10% Pd/C (1.3 g). The mixture was refluxed overnight, then cooled and filtered though a pad of celite. The filtrate was concentrated under vacuum and purified by chromatography on a silica gel column with 0-10% methanol/dichloromethane to provide the title compound (1.2 g, 17%). MS (ESI) m/e 317 (M+H)$^+$.

EXAMPLE 3B 2-(4'-formylbipheny-4-yl)-1H-benzimidazole-4-carboxamide

A solution of EXAMPLE 3A (1.18 g, 3.8 mmol) and 4-formylphenylboronic acid (0.57 g, 3.8 mmol) in dioxane (15 mL) was treated with [1,1'-bis(diphenylphosphino)ferrocene]dichloro palladium (0.32 g, 0.4 mmol) and sodium carbonate (1.8 g, 17 mmol). The mixture was heated at 95° C. for 24 hours, then cooled and filtered. The filtrate was concentrated to provide the crude product, which was used without further purification. MS (ESI) m/e 342 (M+H)$^+$.

EXAMPLE 3C

2-{4'-[(cyclohexylmethylamino)methyl]biphenyl-4-yl}-1H-benzimidazole-4-carboxamide The title compound was prepared as the trifluoroacetate salt using the procedure as described in EXAMPLE 1B, substituting EXAMPLE 3B for EXAMPLE 1A. $^1$H NMR (DMSO-$d_6$) δ 9.33 (s, 1H), 8.35 (t, J=7.5 Hz, 2H), 7.86-7.93 (m, 2H), 7.78 (s, 3H), 7.73-7.78 (m, 2H), 7.66 (d, J=8.3 Hz, 2H) 7.36 (t, J=7.82 Hz, 1H), 4.49 (s, 1H), 4.18-4.47 (m, 1H), 3.25 (s, 1H), 2.65 (d, J=4.6 Hz, 3H), 2.10 (m, 2H), 1.85 (s, 2H), 1.61 (s, 1H), 1.47-1.56 (m, 1H), 1.24-1.32 (m, 1H), 1.18 (s, 1H).

EXAMPLE 4

2-(4'-cyclopropylaminomethylbiphenyl-4-yl)-1H-benzimidazole-4-carboxamide

The title compound was prepared as the trifluoroacetate salt using the procedure as described in EXAMPLE 1B, substituting EXAMPLE 3B for EXAMPLE 1A and cyclopropylamine for cyclohexylmethylamine. $^1$H NMR (DMSO-D6) δ 9.00 (s, 2H), 8.36 (d, J=8.3 Hz, 2H), 7.95 (d, J=8.3 Hz, 2H), 7.89 (d, J=8.3 Hz, 3H), 7.74-7.78 (m, 2H), 7.64 (d, J=8.3 Hz, 3H) 7.37 (t, J=7.7 Hz, 1H), 4.33 (s, 2H), 2.76 (s, 1H), 0.79-0.86 (m, 4H).

EXAMPLE 5

2-(4'-cyclobutylaminomethylbiphenyl-4-yl)-1H-benzimidazole-4-carboxamide

The title compound was prepared as the trifluoroacetate salt using the procedure as described in EXAMPLE 1B, substituting EXAMPLE 3B for EXAMPLE 1A and cyclobutylamine for cyclohexylmethylamine. $^1$H NMR (DMSO-D6) δ 9.05 (s, 2H), 8.36 (d, J=8.3 Hz, 2H), 7.95 (d, J=8.3 Hz, 2H), 7.89 (d, J=8.3 Hz, 3H), 7.73-7.80 (m, 2H), 7.62 (d, J=8.3 Hz, 2H) 7.37 (t, J=7.83 Hz, 1H), 4.11 (s, 2H), 3.66 (s, 1H), 2.20 (m, 5H), 1.80 (m, 2H).

EXAMPLE 6

2-[5-(1-cyclopropylaminoethyl)thiophen-2-yl]-1H-benzimidazole-4-carboxamide

EXAMPLE 6A

5-acetylthiophene-2-carboxylic acid (2-amino-3-carbamoylphenyl) amide

To a solution of 5-acetylthiophene-2-carboxylic acid (1.80 g, 10.55 mmol) in pyridine (12 mL) and N,N-dimethylformamide (12 mL) was added 1,1'-carbonyldiimidazole (1.88 g, 11.60 mmol) and the mixture stirred at 45° C. for 4 hours. 2,3-Diaminobenzamide dihydrochloride (synthesized as described in U.S. Pat. No. 6,737,421, column 11, EXAMPLE 2, step (e), 2.36 g, 10.55 mmol) was added and the mixture was stirred at ambient temperature overnight. The reaction mixture was concentrated and the residue partitioned between ethyl acetate and water. The resulting yellow solid was collected by filtration, washed with water and ethyl acetate and dried to give the title compound (2.91 g, 91%). MS (APCI): 304 (M+1)$^+$.

EXAMPLE 6B

2-(5-acetylthiophen-2-yl)-1H-benzimidazole-4-carboxamide

To a solution of EXAMPLE 6A (1.70 g) in hot N,N-dimethylformamide (60 mL) was added acetic acid (50 mL) and the solution heated at 125° C. for 3 hours. After cooling, the resulting yellow solid was collected by filtration, washed with methanol and dried to give the title compound (1.52 g, 95%). MS (APCI): 286 (M+1)$^+$.

EXAMPLE 6C

2-[5-(1-cyclopropylaminoethyl)thiophen-2-yl]-1H-benzimidazole-4-carboxamide EXAMPLE 6B (100 mg, 0.35 mmol) was dissolved in dimethyl sulfoxide (3 mL) with heating. After cooling to ambient temperature, cyclopropylamine (49 μL, 0.70 mmol) was added. The solution was stirred at ambient temperature overnight and zinc chloride (48 mg, 0.35 mmol) was added. After an additional 1 hour stirring, sodium cyanoborohydride (44 mg, 0.70 mmol) was added and the mixture stirred at ambient temperature for 3 hours. Methanol (3 mL) was added and the solution heated at 80° C. for 2 days. The reaction mixture was concentrated and the residue suspended in water. Trifluoroacetic acid was added with stirring until a transparent solution formed. This solution was filtered and purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt (65.8 mg). $^1$H NMR (CD$_3$OD): δ 0.78-0.84 (m, 1H), 0.86-0.97 (m, 3 H), 1.85 (d, J=7.1 Hz, 3H), 2.69-2.75 (m, 1H), 4.95 (q, J=6.8 Hz, 1H), 7.39 (t, J=7.8 Hz, 1H), 7.44 (d, J=3.7 Hz, 1H), 7.74 (d, J=7.1 Hz, 1H), 7.84 (d, J=4.0 Hz, 1H), 7.95 (d, J=6.8 Hz, 1H).

EXAMPLE 7

2-{5-[1-(cyclohexylmethylamino)ethyl]thiophen-2-yl}-1H-benzimidazole-4-carboxamide The title compound was prepared as the trifluoroacetic acid salt using the procedure as described in EXAMPLE 6C, substituting cyclohexylmethylamine for cyclopropylamine. $^1$H NMR (CD$_3$OD): δ 0.92-1.09 (m, 2H), 1.17-1.37 (m, 3H), 1.64-1.85 (m, 1H), 2.76 (dd, J=12.4, 7.2 Hz, 1H), 2.91 (dd, J=12.6, 6.75 Hz, 1H), 4.78-4.86 (m, 1H), 7.37-7.43 (m, 2H), 7.74 (d, J=8.0 Hz, 1H), 7.83 (d, J=3.7 Hz, 1H), 7.95 (d, J=7.7 Hz, 1H).

EXAMPLE 8

2-(3'-cyclopropylaminomethylbiphenyl-4-yl)-1H-benzimidazole-4-carboxamide

EXAMPLE 8A

2-(3'-formylbipheny-4-yl)-1H-benzimidazole-4-carboxamide

The title compound was prepared using the procedure as described in EXAMPLE 3B, substituting 3-formylphenylboronic acid for 4-formyl-phenylboronic acid. MS (ESI) m/e 342 (M+H)$^+$.

EXAMPLE 8B

2-(3'-cyclopropylaminomethylbiphenyl-4-yl)-1H-benzimidazole-4-carboxamide

The title compound was prepared using the procedure as described in EXAMPLE 1B, substituting EXAMPLE 8A for EXAMPLE 1A and cyclopropylamine for cyclohexylmethylamine. $^1$H NMR (DMSO-D6) δ 9.38 (d, J=3.0 Hz, 1H), 8.34 (d, J=8.5 Hz, 2H), 7.88-7.93 (m, 3H), 7.74-7.81 (m, 3H), 7.66 (d, J=7.6 Hz, 1H) 7.46 (t, J=7.5 Hz, 1H), 7.35-741 (m, 2H), 3.88 (s, 2H), 3.29 (m, 1H), 0.42 (d, J=4.9 Hz, 2H), 0.36 (s, 2H).

EXAMPLE 9

2-(2'-cyclopropylaminomethylbiphenyl-4-yl)-1H-benzimidazole-4-carboxamide

EXAMPLE 9A 2-(2'-formylbipheny-4-yl)-1H-benzimidazole-4-carboxamide

The title compound was prepared using the procedure as described in EXAMPLE 3B, substituting 2-formylphenylboronic acid for 4-formyl-phenylboronic acid. MS (ESI) m/e 342 (M+H)$^+$.

EXAMPLE 9B 2-(2'-cyclopropylaminomethylbiphenyl-4-yl)-1H-benzimidazole-4-carboxamide The title compound was prepared using the procedure as described in EXAMPLE 2, substituting EXAMPLE 9A for EXAMPLE 1A, and cyclopropylamine for cyclobutylamine. $^1$H NMR (DMSO-d$_6$) δ 9.39 (s, 1H), 8.31 (s, 2H), 7.88 (s, 1H), 7.77 (s, 2H), 7.65 (s, 2H), 7.57 (s, 1H), 7.37 (s, 3H), 7.30 (s, 1H), 3.68 (s, 2H), 2.04 (s, 1H), 0.30 (s, 2H), 0.19 (s, 2H).

EXAMPLE 10

2-[3-(2-cyclopropylaminoethyl)phenyl]-1H-benzimidazole-4-carboxamide

EXAMPLE 10A 2-(3-[1,3]dioxolan-2-ylmethylphenyl)-1H-benzimidazole-4-carboxamide A solution of 3-(1,3-dioxolan-2-ylmethyl)benzoic acid (1.0 g, 4.80 mmol) in a mixture of pyridine (5 mL) and N,N-dimethylformamide (5 mL) was treated with 1,1'-carbonyldiimidazole (0.856 g, 5.28 mmol) at 45° C. for 2 hours. 2,3-diaminobenzamide dihydrochloride (synthesized as described in U.S. Pat. No. 6,737,421, column 11, EXAMPLE 2, step (e), 1.08 g, 4.80 mmol) was added and the mixture stirred at ambient temperature overnight. The mixture was concentrated and the residue purified by flash chromatography on silica gel with 10% methanol in 2:1 ethyl acetate/hexane. The product was dissolved in acetic acid (20 mL) and the solution heated at 60° C. for 2 hours and at 80° C. for 1.5 hours, cooled and concentrated and the residue partitioned between ethyl acetate and sodium bicarbonate solution. The organic phase was concentrated and the residue purified on silica gel with 10% methanol in 2:1 ethyl acetate/hexane to give 1.13 g of the title compound. MS (APCI) m/z 324 (M+H)$^+$.

EXAMPLE 10B

2-[3-(2-cyclopropylaminoethyl)phenyl]-1H-benzimidazole-4-carboxamide

A solution of EXAMPLE 10A (300 mg, 0.88 mmol) in acetic acid (10 mL) and water (20 mL) was heated at 70° C. for 20 hours. After cooling, the solution was concentrated to give a light yellow solid. To a solution of the crude aldehyde (80 mg) in dimethyl sulfoxide (2 mL) and methanol (3 mL) was added cyclopropylamine (60 μL) and the mixture stirred at ambient temperature for 1 hour. Sodium cyanoborohydride (54 mg, 0.86 mmol) was added and the mixture heated at 55° C. overnight. Volatiles were removed and the residue purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide 8.8 mg of the title compound as a trifluoroacetate salt. To a solution of this salt in 1:1 methanol/dichloromethane (1 mL) was added 1M HCl in ether (3 mL). Concentration afforded the title compound as a hydrochloride salt. $^1$H NMR (CD$_3$OD): δ 0.91-1.03 (m, 4H), 2.83-2.89 (m, 1H), 3.23-3.29 (m, 2H), 3.49-3.55 (m, 2H), 7.70-7.79 (m, 3H), 8.03-8.13 (m, 3 H), 8.20 (s, 1H),

EXAMPLE 11

2-(4-cyclopropylaminomethylphenyl)-1H-benzimidazole-4-carboxamide

EXAMPLE 11A 2-(4-diethoxymethylphenyl)-1H-benzimidazole-4-carboxamide

To a suspension of 2,3-diaminobenzamide dihydrochloride (synthesized as described in U.S. Pat. No. 6,737,421, column 11, EXAMPLE 2, step (e), 5.0 g, 22.3 mmol) in N,N-dimethylacetamide (DMA, 65 mL) was added lithium hydroxide monohydrate (1.87 g, 44.6 mmol) and the mixture heated at 50° C. for 20 minutes. After cooling, terephthaldehyde mono(diethylacetal) (5.1 g, 24.48 mmol) in N,N-dimethylacetamide (10 mL) and sodium bisulphite (4.81 g, 40.16 mmol) were added. The mixture was heated at 100° C. for 3 hours, cooled and the solvent removed. The residue was partitioned between ethyl acetate and water and the organic layer was washed with brine and concentrated. The residue was purified by flash chromatography on silica gel with ethyl acetate to provide the title compound (4.5 g, 54%). MS (DCI/NH$_3$) m/z 340 (M+H)$^+$.

EXAMPLE 11B 2-(4-formylphenyl)-1H-benzimidazole-4-carboxamide

To a suspension of EXAMPLE 11A (4.5 g, 13.14 mmol) in ethanol (100 mL) and water (100 mL) was added concentrated sulfuric acid (2.9 mL) and the mixture refluxed for 18 hours. The reaction mixture was cooled, partially concentrated, and the residue neutralized with aqueous sodium hydroxide solution. The solid was collected by filtration, washed with water and cold ethanol and dried to provide the title compound (2.5 g, 73%). MS (DCI/NH$_3$) m/z 266 (M+H)$^+$.

EXAMPLE 11C 2-(4-cyclopropylaminomethylphenyl)-1 H-benzimidazole-4-carboxamide A solution of EXAMPLE 11B (100 mg, 0.38 mmol) and cyclopropylamine (43 mg, 0.75 mmol) in 1:1 methanol/N,N-dimethylformamide (5 mL) was stirred at ambient temperature for 2 hours. Sodium cyanoborohydride (47 mg, 0.75 mmol) and zinc chloride (51 mg, 0.38 mmol) were added and the cloudy mixture stirred at ambient temperature for 18 hours. The mixture was concentrated and the residue purified by HPLC (Zorbax C-8, 0.1% trifluoroacetic acid/acetonitrile/ water). The trifluoroacetate salt was dissolved in methanol, treated with anhydrous hydrogen chloride in ether, and concentrated to give the title compound as the hydrochloride salt (41 mg, 35%). $^1$H NMR (CD$_3$OD): δ 0.89-1.03 (m, 4H), 2.77-2.96 (m, 1H), 4.50 (s, 2H), 7.69 (t, J=8.0 Hz, 1H), 7.89 (d, J=8.6 Hz, 2H), 8.01 (d, J=8.3 Hz, 1H), 8.07 (dd, J=7.7, 0.6 Hz, 1H), 8.29 (d, J=8.3 Hz, 2H).

EXAMPLE 12

2-(4-cyclobutylaminomethylphenyl)-1H-benzimidazole-4-carboxamide

The title compound was prepared as the hydrochloride salt (60 mg, 50%) using the procedure as described in EXAMPLE 11C, and substituting cyclobutylamine for cyclopropylamine. $^1$H NMR (CD$_3$OD): δ 1.89-2.04 (m, 2H), 2.23-2.46 (m, 4H), 3.83-3.96 (m, 1H), 4.28 (s, 2H), 7.69 (t, J=8.0 Hz, 1H), 7.87 (d, J=8.3 Hz, 2H), 8.01 (d, J=8.3 Hz, 1H), 8.07 (dd, J=7.7, 0.9 Hz, 1H), 8.29 (d, J=8.6 Hz, 2H).

EXAMPLE 13

2-(4-cyclopentylaminomethylphenyl)-1H-benzimidazole-4-carboxamide

The title compound was prepared as the hydrochloride salt (72 mg, 57%) using the procedure as described in EXAMPLE 11C, substituting cyclopentylamine for cyclopropylamine. $^1$H NMR (CD$_3$OD): δ 1.64-1.83 (m, 4H), 1.83-1.93 (m, 2H), 2.14-2.30 (m, 2H), 3.63-3.76 (m, 1H), 4.39 (s, 2H), 7.69 (t, J=8.0 Hz, 1H), 7.91 (d, J=8.6 Hz, 2H), 8.01 (dd, J=8.3, 0.9 Hz, 1H), 8.07 (dd, J=7.7, 0.9 Hz, 1H), 8.29 (d, J=8.6 Hz, 2H).

EXAMPLE 14

6-chloro-2-{4-[(1,2,3,4-tetrahydronaphthalen-1-ylamino)methyl]phenyl}-1H-benzimidazole-4-carboxamide

EXAMPLE 14A 2-amino-5-chloro-3-nitrobenzamide

Step A

Preparation of 2-amino-3-nitrobenzamide

To a solution of 2-amino-3-nitrobenzoic acid (prepared using the procedure as described in U.S. Pat. No. 6,737,421, EXAMPLE 2, part b) in dimethoxyethane (DME, 7.1 mL/g), was added thionyl chloride (1.33 equivalents). The mixture was stirred at 50° C. for 12 hours, cooled and slowly added to concentrated ammonium hydroxide (22 equivalents). The mixture was stirred at 50° C. for 2 hours, water was added, and the mixture was cooled and filtered. The solid was washed with water and isopropanol, and dried under vacuum to give the title compound (89% yield).

Step B

Preparation of 2-amino-5-chloro-3-nitrobenzamide

A solution of the product of step B (5.0 g, 27.6 mmol) in acetonitrile (1250 mL) was treated with N-chlorosuccinimide (3.87 g, 29 mmol) at 60° C. for 24 hours. After cooling, the solid was collected by filtration, washed with acetonitrile and dried to give the title compound (4.0 g, 67%). MS (DCI/NH$_3$) m/z 216 (M+H)$^+$.

EXAMPLE 14B 2,3-diamino-5-chloro-benzamide

To a solution of EXAMPLE 14A (4.0 g, 18.6 mmol) in tetrahydrofuran (500 mL) and ethanol (500 mL) was added Raney nickel (50% in water, 2.0 g). The mixture was stirred under hydrogen (balloon) at ambient temperature for 6 hours. Solid material was filtered off and the filtrate was concentrated to give the title compound (100% yield). MS (DCI/NH$_3$) m/z 186 (M+H)$^+$.

EXAMPLE 14C 6-chloro-2-(4-diethoxymethylphenyl)-1H-benzimidazole-4-carboxamide The title compound was prepared using the procedure as described in EXAMPLE 11A, substituting EXAMPLE 14B for 2,3-diaminobenzamide dihydrochloride (47% yield). MS (DCI/NH$_3$) m/z 374 (M+H)$^+$.

EXAMPLE 14D 6-chloro-2-(4-formylphenyl)-1H-benzimidazole-4-carboxamide

The title compound was prepared using the procedure as described in EXAMPLE 11B, substituting EXAMPLE 14C for EXAMPLE 11A (82% yield). MS (DCI/NH$_3$) m/z 300 (M+H)$^+$.

EXAMPLE 14E 6-chloro-2-{4-[(1,2,3,4-tetrahydronaphthalen-1-ylamino)methyl]phenyl}-1H-benzimidazole-4-carboxamide The title compound was prepared as the hydrochloride salt (50% yield) using the procedure as described in EXAMPLE 11C, substituting EXAMPLE 14D for EXAMPLE 11B and 1,2,3,4-tetrahydro-1-naphthalene for cyclopropylamine. $^1$H NMR (CD$_3$OD): δ 1.90-2.00 (m, 1H), 2.00-2.10 (m, 1H), 2.18-2.29 (m, 1H), 2.33-2.44 (m, 1H), 2.83-2.93 (m, 1H), 2.95-3.05 (m, 1H), 4.45-4.55 (m, 2H), 4.65 (t, J=5.0 Hz, 1H), 7.26-7.30 (m, 1H), 7.32 (d, J=7.6 Hz, 1H), 7.35-7.39 (m, 1H), 7.50 (d, J=7.6 Hz, 1H), 7.93 (d, J=8.2 Hz, 2H), 8.06 (d, J=1.5 Hz, 1H), 8.13 (d, J=1.8 Hz, 1H), 8.27 (d, J=8.2 Hz, 2H).

EXAMPLE 15

2-(4-cyclopropylaminomethylphenyl)-6-fluoro-1H-benzimidazole-4-carboxamide

EXAMPLE 15A 2-bromo-4-fluoro-6-nitrophenylamine

To a solution of 4-fluoro-2-nitroaniline (20 g, 128 mmol) in dichloromethane (600 mL) and acetic acid (200 mL) was slowly added bromine (13 mL, 256 mmol) at 0° C. The mixture was stirred at 0° C. for 1 hour and at ambient temperature for 16 hours. The mixture was concentrated and the residue partitioned between ethyl acetate and sodium bicarbonate solution. The organic phase was washed with sodium bisulphite solution and concentrated and the residue recrys-

EXAMPLE 15B 2-amino-5-fluoro-3-nitrobenzonitrile

A suspension of EXAMPLE 15A (22.7 g, 96.2 mmol), zinc cyanide (22.6 g, 192 mmol) and palladium tetrakis(triphenylphosphine) (7.78 g, 6.7 mmol) in N,N-dimethylformamide (300 mL) was heated at 80° C. for 22 hours. After cooling, the mixture was partitioned between ethyl acetate and brine and the organic phase washed with water and concentrated. Recrystallization from methanol provided the title compound (13.9 g, 80%). MS (DCI/NH$_3$) m/z 182 (M+H)$^+$.

EXAMPLE 15C 2-amino-5-fluoro-3-nitro-benzamide

A suspension of EXAMPLE 15B (13.9 g, 77 mmol) in polyphosphoric acid (400 g) was stirred at 115° C. for 3 hours. After cooling, water and dichloromethane were added and the mixture stirred at ambient temperature for 30 minutes. The solid was filtered and recrystallized from methanol to give the title compound (11.2 g, 74%). MS (DCI/NH$_3$) m/z 200 (M+H)$^+$.

EXAMPLE 15D 2,3-diamino-5-fluorobenzamide

To a solution of EXAMPLE 15C (1 1.2 g, 56.28 mmol) in tetrahydrofuran (50 mL) and ethanol (50 mL) was added Raney nickel (50% in water, 11.0 g) and the mixture stirred at ambient temperature under hydrogen (60 psi) for 2 hours. The solid material was filtered off and the filtrate concentrated to provide the title compound (9.1 g, 96%). MS (DCI/NH$_3$) m/z 170 (M+H)$^+$.

EXAMPLE 15E 2-(4-diethoxymethylphenyl)-6-fluoro-1H-benzimidazole-4-carboxamide The title compound was prepared using the procedure as described in EXAMPLE 11A, substituting EXAMPLE 15D for 2,3-diaminobenzamide dihydrochloride (50% yield). MS (DCI/NH$_3$) m/z 358 (M+H)$^+$.

EXAMPLE 15F 6-fluoro-2-(4-formylphenyl)-1H-benzimidazole-4-carboxamide

The title compound was prepared using the procedure as described in EXAMPLE 11B, substituting EXAMPLE 15E for EXAMPLE 11A (95% yield). MS (DCI/NH$_3$) m/z 284 (M+H)$^+$.

EXAMPLE 15G 2-(4-cyclopropylaminomethylphenyl)-6-fluoro-1H-benzimidazole-4-carboxamide The title compound was prepared as the hydrochloride salt (14% yield) using the procedure as described in EXAMPLE 11C, substituting EXAMPLE 15F for EXAMPLE 11B. $^1$H NMR (CD$_3$OD): δ 0.91-1.02 (m, 4H), 2.81-2.92 (m, 1H), 4.49 (s, 2H), 7.72 (dd, J=7.6, 2.14 Hz, 1H), 7.86 (d, J=8.2 Hz, 2H), 7.88 (d, J=2.1 Hz, 1H), 8.27 (d, J=8.5 Hz, 2H).

EXAMPLE 16

2-(4-Cyclobutylaminomethylphenyl)-6-fluoro-1H-benzimidazole-4-carboxamide

The title compound was prepared as the hydrochloride salt (22% yield) using the procedure as described in EXAMPLE 11C, substituting EXAMPLE 15F for EXAMPLE 11B and cyclobutylamine for cyclopropylamine. $^1$H NMR (CD$_3$OD): δ 1.89-2.01 (m, 2H), 2.23-2.33 (m, 2H), 2.33-2.44 (m, 2H), 3.83-3.94 (m, 1H), 4.27 (s, 2H), 7.74 (dd, J=7.6, 2.1 Hz, 1H), 7.85 (d, J=8.2 Hz, 2H), 7.88 (dd, J=9.9, 2.3 Hz, 1H), 8.27 (d, J=8.2 Hz, 2H).

EXAMPLE 17

2-(4-Cyclopentylaminomethylphenyl)-6-fluoro-1H-benzimidazole-4-carboxamide

The title compound was prepared as the hydrochloride salt (23% yield) using the procedure as described in EXAMPLE 11C, substituting EXAMPLE 15F for EXAMPLE 11B and cyclopentylamine for cyclopropylamine. $^1$H NMR (CD$_3$OD): δ 1.66-1.82 (m, 4H), 1.82-1.93 (m, 2H), 2.15-2.28 (m, 2H), 3.65-3.69 (m, 1H), 4.39 (s, 2H), 7.75 (dd, J=7.6, 2.1 Hz, 1H), 7.88 (d, J=8.2 Hz, 2H), 7.90 (d, J=2.4 Hz, 1H), 8.27 (d, J=8.5 Hz, 2H).

EXAMPLE 18

2-[4-(2-cyclopropylaminoethyl)phenyl]-1H-benzimidazole-4-carboxamide

The title compound was prepared as the hydrochloride salt using the procedure as described in EXAMPLE 10, substituting 4-(1,3-dioxolan-2-ylmethyl)benzoic acid for 3-(1,3-dioxolan-2-ylmethyl)benzoic acid in EXAMPLE 10A. $^1$H NMR (CD$_3$OD): δ 0.92-1.01 (m, 4H), 2.81-2.88 (m, 1H), 3.21-3.25 (m, 2H), 3.46-3.51 (m, 2H), 7.68-7.73 (m, 3H), 8.02 (d, J=7.6 Hz, 1H), 8.06 (d, J=7.6 Hz, 1H), 8.20 (d, J=7.9 Hz, 2H).

EXAMPLE 19

2-[4-(2-cyclobutylaminoethyl)phenyl]-1H-benzimidazole-4-carboxamide

The title compound was prepared as the hydrochloride salt using the procedure as described in EXAMPLE 10, substituting 4-(1,3-dioxolan-2-ylmethyl)benzoic acid for 3-(1,3-dioxolan-2-ylmethyl)benzoic acid in EXAMPLE 10A and substituting cyclobutylamine for cyclopropylamine in EXAMPLE 10B. $^1$H NMR (CD$_3$OD): δ 1.89-2.00 (m, 2H), 2.24-2.32 (m, 2H), 2.33-2.40 (m, 2H), 3.15-3.21 (m, 2H), 3.22-3.28 (m, 2H), 3.81-3.88 (m, 1H), 7.68-7.73 (m, 3H), 8.02 (d, J=8.2 Hz, 1H), 8.06 (d, J=7.6 Hz, 1H), 8.19 (d, J=8.2 Hz, 2H).

EXAMPLE 20

2-(4-cyclopropylaminomethyl-2-fluorophenyl)-1H-benzimidazole-4-carboxamide

EXAMPLE 20A methyl 4-cyano-2-fluorobenzoate

A solution of methyl 4-bromo-2-fluorobenzoate (10.0 g, 43 mmol), zinc cyanide (10.0 g, 86 mmol) and palladium tetrakis (triphenylphosphine) (2.5 g, 0.64 mmol) in anhydrous N,N-dimethylformamide (100 mL) was purged with nitrogen and the mixture stirred at 80° C. overnight. After cooling, the mixture was partitioned between ethyl acetate and brine and the organic phase washed with water and concentrated. The solid was purified on silica gel using 1:5 ethyl acetate/hexane to afford the title compound (6.1 g, 80%). MS (DCI): m/z 180 $(M+H)^+$.

EXAMPLE 20B methyl 2-fluoro-4-formylbenzoate

EXAMPLE 20A (310 mg, 1.73 mmol) was dissolved in 60% aqueous acetic acid (10 mL) with warming. Raney nickel (60 mg) was added and the mixture was stirred under hydrogen at ambient temperature for 18 hours. Solid material was filtered off and the filtrate concentrated. The residue was purified on silica gel using 1:4 ethyl acetate/hexane to give the title compound (220 mg, 70%). MS (DCI): m/z 183 $(M+H)^+$.

EXAMPLE 20C methyl 4-[1,3]dioxolan-2-yl-2-fluorobenzoate

A solution of EXAMPLE 20B (2.0 g, 11 mmol), 1,2-ethanediol (1.0 g, 16 mmol) and p-toluenesulfonic acid monohydrate (10 mg) in benzene (10 mL) was heated under reflux with a Dean-Stark apparatus for about 6 hours. After cooling, the mixture was partitioned between ethyl acetate and brine and the organic phase washed with 10% sodium hydroxide solution and water. After concentration, the residue was purified by flash chromatography using 1:5 ethyl acetate/hexane to give the title compound (2.1 g, 80%). MS (DCI): m/z 227 $(M+H)^+$.

EXAMPLE 20D

4-[1,3]dioxolan-2-yl-2-fluorobenzoic acid

To a solution of EXAMPLE 20C (2.0 g) in tetrahydrofuran (10 mL) and water (5 mL) was added lithium hydroxide monohydrate (1 g) in water (5 mL). Methanol was added until a transparent solution formed and the solution stirred at ambient temperature for 4 hours and concentrated to about 5 mL. The residue was acidified with 2N HCl to pH 2 and the mixture partitioned between ethyl acetate and water. The organic phase was washed with water, dried over magnesium sulfate, filtered and concentrated to give the title compound (1.5 g, 79%). MS (DCI): m/z 213 $(M+H)^+$.

EXAMPLE 20E 2-(4-[1,3]dioxolan-2-yl-2-fluorophenyl)-1H-benzimidazole-4-carboxamide A solution of EXAMPLE 20D (1.5 g, 7.1 mmol) in pyridine (5 mL) and N,N-dimethylformamide (20 mL) was treated with 1,1'-carbonyldiimidazole (1.4 g, 8.5 mmol) at 40° C. for 30 minutes. 2,3-Diaminobenzamide dihydrochloride (synthesized as described in U.S. Pat. No. 6,737,421, column 11, EXAMPLE 2, step (e), 1.58 g, 7.1 mmol) was added and the mixture stirred at ambient temperature overnight. Solvents were removed and the residue suspended in 10 mL of acetic acid. The mixture was stirred at 80° C. overnight, cooled, and concentrated and the residue was purified by flash chromatography using ethyl acetate to give the title compound (500 mg, 22%). MS (DCI/NH$_3$) m/z 329 $(M+H)^+$.

EXAMPLE 20F 2-(2-fluoro-4-formylphenyl)-1H-benzimidazole-4-carboxamide

A solution of EXAMPLE 20E (500 mg, 1.5 mmol) in acetic acid (5 mL) and water (10 mL) was heated at 80° C. overnight. After cooling, the mixture was concentrated to give the title compound (400 mg, 94%). MS (DCI/NH$_3$) m/z 285 $(M+H)^+$.

EXAMPLE 20G

2-[4-(cyclopropylamino)-2-fluorophenyl]-1H-benzimidazole-4-carboxamide

To a solution of EXAMPLE 20F (85 mg, 0.3 mmol) in N,N-dimethylformamide (5 mL) and methanol (10 mL) was added cyclopropylamine (34 mg, 0.6 mmol) and the solution stirred at ambient temperature for 10 minutes. Sodium cyanoborohydride (38 mg) was added and the mixture heated at 55° C. overnight. After cooling, the mixture was concentrated and the residue purified by HPLC (Zorbax, C-18, 250× 2.54 column, Mobile phase A: 0.1% trifluoroacetic acid in H$_2$O; B: 0.1% trifluoroacetic acid in acetonitrile; 0-100% gradient) to provide the title compound as the trifluoroacetate salt (62 mg). $^1$H NMR (CD$_3$OD) δ 0.96 (d, J=5.5 Hz, 4H); 2.84 (t, J=5.5 Hz, 1H); 4.42 (s, 2H); 7.43 (t, J=7.8 Hz, 1H); 7.47-7.61 (m, 2H); 7.83 (d, J=8.0 Hz, 1H); 7.97 (d, J=7.7 Hz, 1H); 8.38 (t, J=7.8 Hz, 1H).

EXAMPLE 21

2-[4-(1-cyclopropylaminoethyl)phenyl]-1H-benzimidazole-4-carboxamide

A solution of EXAMPLE 1A (0.07 g, 0.3 mmol) and cyclopropylamine (0.33 mL, 4.8 mmol) in methanol (1 mL) was treated with sodium cyanoborohydride (0.016 g, 0.3 mmol) and acetic acid (0.2 mL). The mixture was stirred at ambient temperature for 48 hours and concentrated. The residue was purified by chromatography on silica gel column with 0-10% dichloromethane/methanol/0.1% ammonium hydroxide to provide the title compound. $^1$H NMR (DMSO-d$_6$) δ 9.12 (s, 2H), 8.33 (d, J=8.3 Hz, 2H), 7.88 (d, J=7.4 Hz, 1H), 7.71-7.78 (m, 4H), 7.37 (t, J=7.8 Hz, 1H), 4.59 (m, 1H), 2.57 (s, 1 Hz), 1.64 (d, J=6.6 Hz, 3H), 0.81-0.87 (m, 1H), 0.75-0.79 (m, 1H), 0.66-0.72 (m, 2H).

EXAMPLE 22

2-(4-cyclobutylaminomethyl-2-fluorophenyl]-1H-benzimidazole-4-carboxamide

EXAMPLE 22A methyl 4-[1,3]dioxan-2-yl-2-fluorobenzoate

A solution of 2.0 g (11 mmol) of EXAMPLE 20B, 1.67 g (22 mmol) of 1,3-propanediol, 62 mg (1.1 mmol) of 1,2-ethanediol, 20 mL of benzene and 10 mg of p-toluenesulfonic acid monohydrate was heated at reflux for about 6 hours with a Dean-Stark apparatus until water no longer separated. After cooling, the mixture was partitioned between ethyl acetate and brine and the organic phase washed with 10% sodium hydroxide and water and concentrated. The residue was purified by flash chromatography on silica gel using 1:5 ethyl acetate/hexane) to give the title compound (1.9 g, 73%). MS (DCI): m/z 241 (M+H)$^+$.

EXAMPLE 22B

4-[1,3]dioxan-2-yl-2-fluorobenzoic acid

To a solution of EXAMPLE 22A (1. 9 g) in tetrahydrofuran (10 mL) and water (5 mL) was added lithium hydroxide (1 g) in water (5 mL). Methanol was added until homogeneous and the solution stirred at ambient temperature for 4 hours. The mixture was concentrated to 5 mL and the residue acidified to pH 2 with 2 N hydrochloric acid. Ethyl acetate and water were added and the organic phase separated, washed with water, dried over magnesium sulfate, filtered and concentrated to give the title compound (1.7g, 95%). MS (DCI): m/z 227 (M+H)$^+$.

EXAMPLE 22C 2-(4-[1,3]dioxan-2-yl-2-fluorophenyl)-1H-benzimidazole-4-carboxamide A solution of EXAMPLE 22B (770 mg, 3.4 mmol) in pyridine (5 mL) and N,N'-dimethylformamide (10 mL) was treated with 1,1'-carbonyldiimidazole (763 mg, 3.4 mmol) at 40° C. for 30 minutes. 2,3-Diaminobenzamide dihydrochloride (826 mg, 5.1 mmol) was added and the mixture stirred at ambient temperature overnight. The mixture was concentrated and the residue refluxed overnight in 20 mL of xylene and 2 mL of acetic acid. After cooling and concentration, the residue was purified by flash chromatography on silica gel using ethyl acetate to give the title compound (550 mg, 50%). MS (DCI/NH$_3$) m/z 342 (M+H)$^+$.

EXAMPLE 22D 2-(2-fluoro-4-formylphenyl)-1H-benzimidazole-4-carboxamide

A solution of EXAMPLE 22C (550 mg, 1.6 mmol) in acetic acid (5 mL) and water (10 mL) was heated at 70° C. overnight. After cooling, the mixture was concentrated to give the title compound (430 mg, 93%). MS (DCI/NH$_3$) m/z 285 (M+H)$^+$.

EXAMPLE 22

2-(4-cyclobutylaminomethyl-2-fluorophenyl)-1H-benzimidazole-4-carboxamide

To a suspension of EXAMPLE 22D (50 mg, 0.17 mmol) in methanol (10 mL) was added cycolobutylamine (36 mg, 0.5 mmol) and the mixture stirred at 50° C. for 4 hours. Sodium cyanoborohydride (38 mg) was added and the mixture heated at 55° C. overnight. After cooling, the mixture was concentrated and the residue purified by HPLC (Zorbax, C-18, 250× 2.54 column, Mobile phase A: 0.1% trifluoroacetic acid in water; B: 0.1% trifluoroacetic acid in acetonitrile; 0-100% gradient) to provide the title compound as the trifluoroacetate salt (62 mg). $^1$H NMR (DMSO-D$_6$): δ 1.70-1.96 (m, 2H); 2.09-2.33 (m, 4H); 3.77 (t, J=7.1 Hz, 1H); 4.18 (s, 2H); 7.40 (t, J=7.8 Hz, 1H); 7.55 (dd, J=8.0, 1.5 Hz, 1H); 7.65 (dd, J=12.1, 1.4 Hz, 1H); 7.78 (s, 1H); 7.84 (d, J=8.0 Hz, 1H); 7.93 (d, J=8.0 Hz, 1H); 8.38 (t, J=8.0 Hz, 1H); 9.14 (s, 1H) 9.34 (s, 2H).

EXAMPLE 23

2-(4-cyclohexylaminomethyl-2-fluorophenyl)-1H-benzimidazole-4-carboxamide

The title compound was prepared according to the procedure for EXAMPLE 22, substituting cyclohexylamine for cyclobutylamine. $^1$H NMR (DMSO-D$_6$): δ1.10-1.19 (m, 1H), 1.20-1.41 (m, 4H), 1.63 (br d, J=12.6 Hz, 1H), 1.80 (br d, J=12.9 Hz, 2H), 2.09-2.17 (m, 2H), 3.03-3.11 (m, 1H), 4.29-4.34 (m, 2H), 7.40 (t, J=8.0 Hz, 1H), 7.57 (dd, J=8.3, 1.5 Hz, 1H), 7.66 (dd, J=12.3, 1.2 Hz, 1H), 7.77 (br s, 1H), 7.82 (d, J=8.0 Hz, 1H), 7.92 (d, J=8.3, 1H), 8.39 (t, J=8.0 Hz, 1H), 8.94 (br s, 2H), 9.14 (br s, 1H).

EXAMPLE 24

2-(4-cyclopentylaminomethyl-2-fluorophenyl)-1H-benzimidazole-4-carboxamide

The title compound was prepared according to the procedure for EXAMPLE 22, substituting cyclopentylamine for cyclobutylamine. $^1$H NMR (DMSO-d$_6$): δ 1.51-1.62 (m, 2H), 1.65-1.78 (m, 4H), 1.96-2.08 (m, 2H), 3.51-3.60 (m, 1H), 4.26-4.33 (m, 2H), 7.41 (t, J=7.7 Hz, 1H), 7.59 (d, J=8.0 Hz, 1H), 7.68 (d, J=12.3 Hz, 1H), 7.78 (br s, 1H), 7.84 (d, J=8.0 Hz, 1H), 7.93 (d, J=7.7 Hz, 1H), 8.38 (t, J=7.8 Hz, 1H), 9.15 (br s, 2H),).

EXAMPLE 25

2-{2-[(cyclopentylamino)methyl]-1,3-thiazol-4-yl}-1H-benzimidazole-4-carboxamide

EXAMPLE 25A ethyl 2-({[(benzyloxy)carbonyl]amino}methyl)-1,3-thiazole-4-carboxylate To a solution of N-benzyloxycarbonylglycine thioamide (1.49 g, 6.64 mmol) in 1,2-dimethoxyethane (25 mL) was added potassium hydrogen carbonate (2.66 g, 26.56 mmol) and ethylbromopyruvate (3.47 mL, 27.54 mmol) at −20° C. and the mixture stirred at −20° C. overnight. The mixture was filtered through a pad of celite and the filtrate was concentrated and the residue was dissolved in 1,2-dimethoxyethane. After cooling to −20° C., a solution of trifluoroacetic anhydride (2.85 mL, 20.52 mmol) and 2,6-lutidine (5.14 mL, 44.29 mmol) in 1,2-dimethoxyethane (10 mL) was added dropwise over 10 minutes. After stirring for 45 minutes, the solution was concentrated and partitioned between chloroform and water. The organic layer was concentrated and the residue was purified by flash chromatography on silica gel eluting with 60% ethyl acetate in hexanes to provide the title product (1.8 g, 85%): MS (DCI/NH$_3$) m/z 321 (M+H)$^+$.

EXAMPLE 25B 2-({[(benzyloxy)carbonyl]amino}methyl)-1,3-thiazole-4-carboxylic acid To a solution of EXAMPLE 25A (1.8 g, 5.62 mmol) in a 5:1 mixture of methanol and water (120 mL) was added lithium hydroxide monohydrate (1.18 g, 28.09 mmol) and the mixture stirred at ambient temperature for 16 hours. The mixture was partially concentrated and the residue brought to pH 2 using 2M hydrochloric acid. The mixture was partitioned between ethyl acetate and brine and the organic phase was washed with water, dried over magnesium sulfate, filtered and concentrated to provide the title compound (1.23 g, 75%): MS (DCI/NH$_3$) m/z 293 (M+H)$^+$.

EXAMPLE 25C benzyl {4-[4-(aminocarbonyl)-1H-benzimidazol-2-yl]-1,3-thiazol-2-yl}methylcarbamate A solution of EXAMPLE 25B (1.7 g, 5.82 mmol) in N,N-dimethylformamide (20 mL) and pyridine (20 mL) was treated with 1,1'-carbonyldiimidazole (990 mg, 6.11 mmol) at 50° C. for 2 hours. 2,3-Diaminobenzamide dihydrochloride (1.3 g, 5.82 mmol) was added and the mixture stirred at ambient temperature for 16 hours. The mixture was concentrated and the residue was dissolved in acetic acid (50 mL) and heated at 100° C. for 2 hours. After cooling, the solution was concentrated and the residue was partitioned between ethyl acetate and saturated sodium bicarbonate. The organic phase was washed with water and concentrated and the residue was purified by flash chromatography on silica gel using 70% ethyl acetate in hexanes to provide the title compound (1.75 g, 74%): MS (DCI/NH$_3$) m/z 408 (M+H)$^+$.

EXAMPLE 25D

2-[2-(aminomethyl)-1,3-thiazol-4-yl]-1H-benzimidazole-4-carboxamide

A solution of EXAMPLE 25C (1.7 g, 4.17 mmol) in trifluoroacetic acid (15 mL) was heated at 50° C. for 16 hours. The mixture was cooled and concentrated and the residue purified by HPLC (Zorbax C-18, 0.1% trifluoroacetic acid/acetonitrile/water) to provide the product as the trifluoroacetate salt. The salt was dissolved in methanol and a solution of 1.8 M hydrochloric acid in diethyl ether (30 mL) added. Concentration afforded the title compound as the hydrochloride salt (910 mg, 80%): MS (DCI/NH$_3$) m/z 274 (M+H)$^+$.

EXAMPLE 25E

2-{2-[(cyclopentylamino)methyl]-1,3-thiazol-4-yl}-1H-benzimidazole-4-carboxamide To a solution of EXAMPLE 25D (50 mg, 0.18 mmol) in methanol (5 mL) was added cyclopentanone (32 μL, 0.36 mmol) and triethylamine (25 μL). The solution was stirred at ambient temperature for 1 hour and sodium cyanoborohydride (34 mg, 0.54 mmol) was added. After stirring for 60 hours, the mixture was concentrated and the residue purified by HPLC (Zorbax C-18, 0.1% trifluoroacetic acid/acetonitrile/water) to provide the title compound as the trifluoroacetate salt. The salt was dissolved in methanol and a solution of 1.8 M hydrochloric acid in diethyl ether (30 mL) was added. Concentration afforded the title compound as the hydrochloride salt (16 mg, 20%): $^1$HNMR (CD$_3$OD) δ 1.71-1.77 (m, 2H), 1.79-1.87 (m, 2H), 1.87-1.95 (m, 2H), 2.21-2.30 (m, 2H), 3.79-3.88 (m, 1H), 4.83 (s, 2H), 7.71 (t, J=7.9 Hz, 1H), 8.05 (d, J=8.2 Hz, 1H), 8.09 (d, J=7.0 Hz, 1H), 9.10 (s, 1H).

EXAMPLE 26

2-{2-[(cyclohexylamino)methyl]-1,3-thiazol-4-yl}-1H-benzimidazole-4-carboxamide

The title compound was prepared as a HCl salt according to procedure described in EXAMPLE 25E, substituting cyclohexanone for cyclopentanone. $^1$H NMR (CD$_3$OD) δ 1.25-1.34 (m, 1H), 1.38-1.48 (m, 2H), 1.48-1.57 (m, 2H), 1.76 (d, J=12.8 Hz, 1H), 1.95 (d, J=13.4 Hz, 2H), 2.28 (d, J=11.9 Hz, 2H), 3.32-3.41 (m, 1H), 4.84 (s, 2H), 7.70 (t, J=7.9 Hz, 1H), 8.03 (d, J=7.3 Hz, 1H), 8.08 (d, J=7.6 Hz, 1H), 9.07 (s, 1H).

EXAMPLE 27

2-{2-[(cyclobutylamino)methyl]-1,3-thiazol-4-yl}-1H-benzimidazole-4-carboxamide

The title compound was prepared as a HCl salt according to procedure described in EXAMPLE 25E, substituting cyclobutanone for cyclopentanone. Yield: 11%. $^1$H NMR (CD$_3$OD) δ 1.93-2.05 (m, 2H), 2.30-2.38 (m, 2H), 2.39-2.47 (m, 2H), 4.00-4.10 (m, 1H), 4.70 (s, 2H), 7.69 (t, J=7.9 Hz, 1H), 8.03 (d, J=8.2 Hz, 1H), 8.08 (d, J=7.6 Hz, 1H), 9.06 (s, 1H).

What is claimed is:

1. A compound of Formula (I)

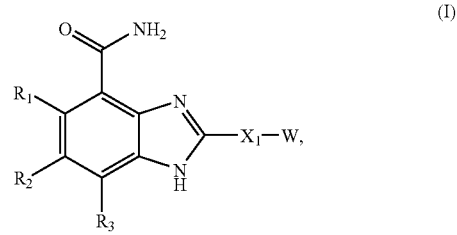

or a therapeutically acceptable salt, thereof, wherein
$R_1$, $R_2$, and $R_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_A R_B$, and $(NR_A R_B)$carbonyl;
$X_1$ is selected from the group consisting of aryl and heteroaryl, wherein $X_1$ is optionally substituted with 1, 2, 3, or 4 substituents selected from the group consisting of alkyl, cyano, halogen, and haloalkyl;

W is $X_2$—Y—$NR_6R_7$ or Y—$NR_6R_7$;

$X_2$ is selected from the group consisting of aryl and heteroaryl, wherein $X_2$ is optionally substituted with 1, 2, 3, or 4 substituents selected from the group consisting of alkyl, cyano, halogen, and haloalkyl;

Y is alkylenyl;

$R_6$ is selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heterocycle, heterocyclealkyl, heteroaryl, heteroarylalkyl, hydroxyalkyl, ($NR_CR_D$)alkyl, ($NR_CR_D$)carbonyl, ($NR_CR_D$)carbonylalkyl, and ($NR_CR_D$)sulfonyl;

$R_7$ is selected from the group consisting of cycloalkyl and cycloalkyl fused to phenyl, wherein $R_7$ may be optionally substituted with 1, 2, or 3 substituents selected from the group consisting of alkenyl, alkoxy, alkoxyalkyl, alkoxycarbonyl, alkoxycarbonylalkyl, alkyl, alkylcarbonyl, alkylcarbonylalkyl, alkynyl, carboxy, cycloalkyl, cycloalkylalkyl, cyano, haloalkoxy, haloalkyl, halogen, hydroxy, hydroxyalkyl, $NR_CR_D$, ($NR_CR_D$)alkyl, ($NR_CR_D$)carbonyl, ($NR_CR_D$)carbonylalkyl, ($NR_CR_D$)sulfonyl, and oxo; and $R_A$, $R_B$, $R_C$, and $R_D$ are independently selected from the group consisting of hydrogen, alkyl, and alkycarbonyl.

2. A compound of Formula (I)

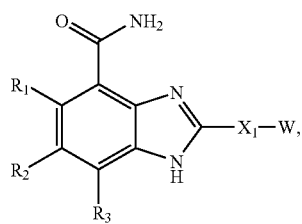

(I)

or a therapeutically acceptable salt, thereof, wherein $R_1$, $R_2$, and $R_3$ are independently selected from the group consisting of hydrogen and halogen;

$X_1$ is selected from the group consisting of aryl and heteroaryl, wherein $X_1$ is optionally substituted with halogen;

W is $X_2$—Y—$NR_6R_7$ or Y—$NR_6R_7$;

$X_2$ is aryl;

Y is alkylenyl;

$R_6$ is selected from the group consisting of hydrogen and alkyl; and $R_7$ is selected from the group consisting of cycloalkyl and cycloalkyl fused to phenyl.

3. A compound according to claim 1, wherein $R_1$, $R_2$, and $R_3$ are hydrogen.

4. A compound according to claim 1, wherein W is Y—$NR_6R_7$.

5. A compound according to claim 1, wherein $R_6$ is hydrogen; and $R_7$ is cycloalkyl.

6. A compound according to claim 1, wherein $X_1$ is thiophenyl.

7. A compound according to claim 1, wherein $X_1$ is thiazolyl.

8. A compound according to claim 1, wherein $X_1$ is phenyl.

9. A compound according to claim 1, wherein $X_1$ is phenyl and $X_2$ is phenyl.

10. A compound according to claim 1 wherein $R_2$ is halogen.

11. A compound or a therapeutically acceptable salt, thereof, selected from the group consisting of
2-{4-[1-(cyclohexylmethylamino)ethyl]phenyl}-1H-benzimidazole-4-carboxamide;
2-[4-(1-cyclobutylaminoethyl)phenyl]-1H-benzimidazole-4-carboxamide;
2-{4'-[(cyclohexylmethylamino)methyl]biphenyl-4-yl}-1H-benzimidazole-4-carboxamide;
2-(4'-cyclopropylaminomethylbiphenyl-4-yl)-1H-benzimidazole-4-carboxamide;
2-(4'-cyclobutylaminomethylbiphenyl-4-yl)-1H-benzimidazole-4-carboxamide;
2-[5-(1-cyclopropylaminoethyl)thiophen-2-yl]-1H-benzimidazole-4-carboxamide;
2-{5-[1-(cyclohexylmethylamino)ethyl]thiophen-2-yl}-1H-benzimidazole-4-carboxamide;
2-(3'-cyclopropylaminomethylbiphenyl-4-yl)-1H-benzimidazole-4-carboxamide;
2-(2'-cyclopropylaminomethylbiphenyl-4-yl)-1H-benzimidazole-4-carboxamide;
2-[3-(2-cyclopropylaminoethyl)phenyl]-1H-benzimidazole-4-carboxamide;
2-(4-cyclopropylaminomethylphenyl)-1H-benzimidazole-4-carboxamide;
2-(4-cyclobutylaminomethylphenyl)-1H-benzimidazole-4-carboxamide;
2-(4-cyclopentylaminomethylphenyl)-1H-benzimidazole-4-carboxamide;
6-chloro-2-{4-[(1,2,3,4-tetrahydronaphthalen-1-ylamino)methyl]phenyl}-1H-benzimidazole-4-carboxamide;
2-(4-cyclopropylaminomethylphenyl)-6-fluoro-1H-benzimidazole-4-carboxamide;
2-(4-Cyclobutylaminomethylphenyl)-6-fluoro-1H-benzimidazole-4-carboxamide;
2-(4-Cyclopentylaminomethylphenyl)-6-fluoro-1H-benzimidazole-4-carboxamide;
2-[4-(2-cyclopropylaminoethyl)phenyl]-1H-benzimidazole-4-carboxamide;
2-[4-(2-cyclobutylaminoethyl)phenyl]-1H-benzimidazole-4-carboxamide;
2-(4-cyclopropylaminomethyl-2-fluorophenyl)-1H-benzimidazole-4-carboxamide;
2-[4-(1-cyclopropylaminoethyl)phenyl]-1H-benzimidazole-4-carboxamide;
2-(4-cyclobutylaminomethyl-2-fluorophenyl)-1H-benzimidazole-4-carboxamide;
2-(4-cyclohexylaminomethyl-2-fluorophenyl)-1H-benzimidazole-4-carboxamide;
2-(4-cyclopentylaminomethyl-2-fluorophenyl)-1H-benzimidazole-4-carboxamide;
2-{2-[(cyclopentylamino)methyl]-1,3-thiazol-4-yl}-1H-benzimidazole-4-carboxamide;
2-{2-[(cyclohexylamino)methyl]-1,3-thiazol-4-yl}-1H-benzimidazole-4-carboxamide; and
2-{2-[(cyclobutylamino)methyl]-1,3-thiazol-4-yl}-1H-benzimidazole-4-carboxamide.

12. A pharmaceutical composition comprising a compound of Formula (I) of claim 1 or a therapeutically acceptable salt thereof, in combination with a therapeutically acceptable carrier.

13. A method of treating inflammation in a mammal in recognized need of such treatment comprising administering to the mammal a therapeutically effective amount of a compound of Formula (I) of claim 1 or a therapeutically acceptable salt thereof.

14. A method of treating sepsis in a mammal in recognized need of such treatment comprising administering to the mammal a therapeutically effective amount of a compound of Formula (I) of claim 1 or a therapeutically acceptable salt thereof.

15. A method of treating septic shock in a mammal in recognized need of such treatment comprising administering to the mammal a therapeutically effective amount of a compound of Formula (I) of claim 1 or a therapeutically acceptable salt thereof.

* * * * *

UNITED STATES PATENT AND TRADEMARK OFFICE
CERTIFICATE OF CORRECTION

| | | |
|---|---|---|
| PATENT NO. | : 7,462,724 B2 | Page 1 of 2 |
| APPLICATION NO. | : 11/560166 | |
| DATED | : December 9, 2008 | |
| INVENTOR(S) | : Penning et al. | |

It is certified that error appears in the above-identified patent and that said Letters Patent is hereby corrected as shown below:

Title Page Column 2 (Other Publications)

Line 13-14:

Delete "poly (ADP-rose)" and insert -- poly (ADP-ribose) --

Line 14

Delete "Ii" and insert -- II --

Line 14

Delete "arthristis" and insert -- arthritis --

Line 19

Delete "arthritis," and insert -- arthritis --

Line 29

Delete "Ptentiation" and insert -- "Potentiation --

Line 31

Delete "carboxamilde" and insert -- carboxamide --

Column 34

Line 60

In Claim 1, delete "salt," and insert -- salt --

Column 35

Line 27

In Claim 1, delete "alkycarbonyl." and insert -- alkylcarbonyl."

Line 41

In Claim 2, delete "salt," and insert -- salt --

Signed and Sealed this
Fourth Day of October, 2011

David J. Kappos
*Director of the United States Patent and Trademark Office*

CERTIFICATE OF CORRECTION (continued)
U.S. Pat. No. 7,462,724 B2

Column 36

Line 3

In Claim 11, delete "salt," and insert -- salt --